US007314709B2

(12) United States Patent
Marnett et al.

(10) Patent No.: US 7,314,709 B2
(45) Date of Patent: Jan. 1, 2008

(54) COMPOSITIONS AND METHODS FOR DETECTING AND QUANTIFYING COX-2 ACTIVITY BY LIPOAMINO ACID METABOLISM

(75) Inventors: Lawrence J. Marnett, Nashville, TN (US); Jeffery J. Prusakiewicz, Nashville, TN (US); Kevin R. Kozak, Nashville, TN (US); Philip J. Kingsley, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 712 days.

(21) Appl. No.: 10/213,633

(22) Filed: Aug. 6, 2002

(65) Prior Publication Data

US 2004/0029207 A1 Feb. 12, 2004

(51) Int. Cl.
  *C12Q 1/00* (2006.01)
  *G01N 33/573* (2006.01)
  *G01N 33/53* (2006.01)
(52) U.S. Cl. .......................... 435/4; 435/7.4; 435/7.91
(58) Field of Classification Search ..................... 435/4
  See application file for complete search history.

(56) References Cited

U.S. PATENT DOCUMENTS

| | | | |
|---|---|---|---|
| 3,632,627 A | 1/1972 | Gordon et al. | |
| 4,675,281 A | 6/1987 | Lands et al. | |
| 5,047,354 A | 9/1991 | Foegh et al. | |
| 5,162,504 A | 11/1992 | Horoszewicz | |
| 5,459,239 A | 10/1995 | O'Neill et al. | |
| 5,474,903 A | 12/1995 | Huland | |
| 5,475,021 A | 12/1995 | Marnett et al. | |
| 5,543,297 A | 8/1996 | Cromlish et al. | |
| 5,589,575 A | 12/1996 | Cohen et al. | |
| 5,700,654 A | 12/1997 | Roberts et al. | |
| 5,731,343 A | 3/1998 | Feng et al. | |
| 5,756,092 A | 5/1998 | Michelet et al. | |
| 5,837,479 A | 11/1998 | Young et al. | |
| 5,858,694 A | 1/1999 | Piazza et al. | |
| 5,858,696 A | 1/1999 | Roberts et al. | |
| 5,874,235 A | 2/1999 | Chan et al. | |
| 5,891,622 A | 4/1999 | Morrow et al. | |
| 5,945,675 A | 8/1999 | Malins | |
| 5,958,978 A | 9/1999 | Yamazaki et al. | |
| 5,973,191 A | 10/1999 | Marnett et al. | |
| 5,995,645 A | 11/1999 | Soenksen et al. | |
| 5,999,843 A | 12/1999 | Anbar | |
| 6,045,773 A | 4/2000 | Isakson et al. | |
| 6,107,049 A | 8/2000 | Allard et al. | |

FOREIGN PATENT DOCUMENTS

| | | |
|---|---|---|
| CA | 71-125851 | 8/1973 |
| DE | 2155546 | 5/1972 |
| FR | 2159202 | 7/1973 |

OTHER PUBLICATIONS

Prusakiewicz et al (BBRC,2002, 296:612-617).*
Wikipedia, the free encyclopedia (On-line reference at http://en.wikipedia.org/wiki/Eicosanoid).*
Kalgutar, et al.; Biochemically based design of cyclooxygenase-2 (COX-2) inhibitors: Facile conversion of nonsteroidal antiinflammatory drugs to potent and highly selective COX-2 inhibitors; PNAS Jan. 18, 2000; 97(2) 925-930.
Kozak, et al.; Oxygenation of the Endocannabinoid, 2-Arachidonylglycerol, to Glyceryl Prostaglandins by Cyclooxygenase-2; The Journal of Biological Chemistry Oct. 27, 2000; 43:33744-33749.
Kozak, et al.; Amino Acid Determinants in Cyclooxygenase-2 Oxygenation of the Endocannabinoid 2-Arachidonylglycerol; JBP Papers in Press Jun. 11, 2001.
Lands, et al.; Phospholipid precursors of prostaglandins; Biochem. Biophys. Acta 1968; 164:426-429.
Prescott; A thematic series on oxidation of lipids as a source of messengers; J. Biol. Chem.; 274:22901.
Smith, et al.; Prostaglandin Endoperoxide H Synthases (Cyclooxygenases)- 1 and -2; The Journal of Biological Chemistry Dec. 27, 1996; 271:52:33157-33160.
So, et al.; The dynamics of prostaglandin H synthases. Studies with prostaglandin h synthase 2 Y355F unmask mechanisms of time-dependent inhibition and allosteric activation; J. Biol. Chem; 273:5801-5807.
Tanha, et al.; Optimal Design Features of Camelized Human Single-Domain Antibody Libraries; JBP Papers in Press May 2, 2001.
Tokumoto, et al.; Specificity of Prostagland D2 Binding to Synaptic Membrane Fraction of Rat Brain; Brain Research 1986; 362:114-121.

(Continued)

*Primary Examiner*—Susan Ungar
(74) *Attorney, Agent, or Firm*—Stites & Harbison PLLC; Richard S. Myers, Jr.

(57) ABSTRACT

A method of detecting an activity of a COX-2 enzyme in a subject that includes obtaining a sample of the subject; detecting an amino acid eicosanoid metabolite in the sample, wherein the presence of the amino acid eicosanoid metabolite indicates the activity of the COX-2 enzyme of the subject. Preferably the amino acid eicosanoid metabolite is a $PGH_2$-Gly or HETE-Gly metabolite. The metabolite may be detected based on metabolism of a COX-2-selective substrate. Preferably, the substrate is a lipoamino acid. More preferably, the lipoamino acid is selected from NAGly, N-arachidonyl-alanine, and δ-arachidonyl aminobutuyic acid.

10 Claims, 3 Drawing Sheets

OTHER PUBLICATIONS

Tsujii, et al.; Cyclooxygenase-2 expression in human colon cancer cells increases metastatic potential; Proc. Natl Acad. Sci. Apr. 1997; 94:3336-3340.

Vonkeman, et al.; The action of prostaglandin synthetase on 2-arachidonyl-lecithin; Biochem. Biophys. Acta; 164:430-432.

Woodward, et al.; The pharmacology of bimatoprost (Lumigan); Surv. Ophthalmol.; 45 Suppl 4; S334-345.

Yu, et al; Synthesis of Prostaglandin E2 Ethanolamide from Anandamide by Cyclooxygenase-2; The Journal of Biological Chemistry Aug. 22, 1997; 272(34):21181-21186.

Cromlish, W.A., et al.; High-Level Expression of Active Human Cyclooxygenase-2 in Insect Cells; Arch. Biochem. Biophys; Oct. 1994; vol. 314; No. 1; pp. 193-199.

Shappel, S.B., et al.; Alterations in Lipoxygenase and Cyclooxygenase-2 Catalytic Activity and mRNA Expression in Prostate Carcinoma; Neoplasia; Jul.-Aug. 2001; vol. 3; No. 4; pp. 287-303.

Mitchell, J.A., et al.; Induction of Cyclo-Oxygenase-2 by Cytokines in Human Pulmanry Epithelial Cells; Regulation by Dexamethason; Br. J. Pharmacol; Nov. 1994; vol. 113.; No. 3; pp. 1008-1114.

* cited by examiner

COMPOSITIONS AND METHODS FOR DETECTING AND QUANTIFYING COX-2 ACTIVITY BY LIPOAMINO ACID METABOLISM

GOVERNMENT SUPPORT CLAUSE

This invention was made with federal grant money from National Institutes of Health grant number CA89450. The United States Government has certain rights in this invention.

This application claims priority to U.S. patent application Ser. Nos. 09/924,082, currently pending and 09/923,637, now U.S. Pat. No. 7,189,504 both of which were filed Aug. 7, 2001, and both of which claim benefit of U.S. Patent Application Ser. Nos. 60/223,665 filed Aug. 7, 2000, now abandoned and U.S. Patent Application Ser. No. 60/302,975 filed Jul. 03, 2001, now abandoned. All the related Applications are hereby incorporated herein by reference in their entirety.

BACKGROUND OF THE INVENTION

1. Field of the Invention

The present invention relates generally to the cyclooxygenases and their roles in human pathology, including cancer and inflammation. More particularly, this invention pertains to methods and articles of manufacture for detecting or measuring COX-2 activity by detecting and measuring COX-2 specific enzymatic products.

2. Description of the Related Art

COX is a prostaglandin endoperoxide synthase enzyme (cyclooxygenase, COX, EC 1.14.99.1), which catalyzes the conversion of arachidonic acid to prostaglandin (PG) H2. Two isoforms of COX are known, COX-1 and COX-2. COX-1 is constitutively expressed. COX-2, however, is inducible in a variety of cells, especially those of the central nervous and immune systems (Masferrer et al. 1994, *Proc. Natl. Acad. Sci. USA* 91:3228-3232; Vane et al. 1994, *Proc. Natl. Acad. Sci. USA* 91:2046-2050; Kennedy et al. 1993, *Biochem. Biophys. Res. Commun.* 197:494-500). Certain changes in COX-2 activity are associated with a variety of human inflammatory diseases. These diseases include, but are not limited to, acute appendicitis, asthma, myocardial infarction, certain immunological disease processes, infection, malignancy, endotoxemia and reperfusion injury. In addition, COX-2 inappropriate expression or overexpression is associated with certain types of cancers, including, but not limited to, carcinoma of the colon, rectum, stomach, esophagus, lung, and skin. The amount of COX-2 expression is related to the stage or progression of cancer (Fosslien, E, et al. 2000, *Ann. Clin. Lab. Sci.* 30:3-21). COX-2 has become a major pharmaceutical target for developing treatments for these and other diseases.

Nonsteroidal anti-inflammatory drugs prevent hyperalgesia and inflammation by inhibiting the cyclooxygenase-2 (COX-2) catalyzed oxygenation of arachidonic acid to prostaglandin (PG) $H_2$. The lipoamino acid N-arachidonylglycine (NAGly), has also been shown to suppress tonic inflammatory pain, and is naturally present at significant levels in many of the same mammalian tissues that express COX-2. The present inventors have discovered that COX-2 selectively metabolizes NAGly to $PGH_2$ glycine ($PGH_2$-Gly) and hydroxyeicosatetraenoic glycine (HETE-Gly). Site-directed mutagenesis experiments identify the side pocket residues of COX-2, especially Arg-513, as critical determinants of the COX-2 selectivity towards NAGly. Additionally, the present inventors have discovered that NAGly is a charged arachidonyl derivative that is a selective substrate for COX-2, allowing for easier detection in some instances. Accordingly, the present inventors have discovered the role for COX-2 in the regulation of lipoamino acid levels, including NAGly levels, and the formation of a novel class of eicosanoids from NAGly metabolism.

Yu et al. (1997) J. Biol. Chem. 272:21181-21186, describes the enzymatic conversion of arachidonyl ethanolamide (anandamide, AEA), to $PGE_2$-ethanolamide in cell lines expressing COX-2 but not COX-1.

U.S. Pat. No. 5,543,297 to Cromlish et al., describes measuring total COX activity (COX-1 activity and COX-2 activity) in separate samples, with and without a COX-2 specific inhibitor, and then indirectly estimating COX-2 specific activity by subtracting the total COX activity observed with the inhibitor from the total COX activity observed without the inhibitor. One major weakness of this method is that the dynamics of enzymatic inhibition change based upon numerous variables including time, temperature, concentration, specificity, sample preparation, etc.

U.S. Pat. No. 5,475,021 to Marnett et al. describes a method of measuring the activity of purified COX-2 by measuring $O_2$-uptake during catalysis. This method requires purification of the enzyme.

U.S. Pat. No. 6,045,773 to Isakson et al., describes a method for measuring COX-2 activity in a mammal by administering a positron-emitting radioisotope-labeled COX-2 selective binding agent to the mammal and then detecting the label by positron-emission tomography (PET). Weaknesses of this method include the invasive nature and expense of PET equipment. In addition, the method only localizes COX-2 protein but does not detect or measure activity.

Methods of detecting and measuring COX-2 activity are highly desired. What is needed, then, is a less-invasive, direct method of selectively detecting and measuring COX-2 activity in biological samples and whole animals without the need to purify the enzyme.

SUMMARY OF THE INVENTION

The present invention provides, in part, novel compositions, articles of manufacture including assays and kits, and methods for detecting and measuring COX-2 enzymatic activity.

Cyclooxygenases (COXs) perform the committed step in prostaglandin (PG) synthesis by catalyzing the bis-dioxygenation of arachidonic acid (AA) to generate $PGH_2$, the precursor to various PGs and thromboxanes [1]. As stated above, two COX isoforms have been identified that are structurally and mechanistically similar, but differ mainly in their regulation and tissue distribution [2,3]. COX-1 is constitutively expressed in most tissues where it is considered to play a role in various physiologic functions. COX-2 is inducible and tightly regulated by a range of stimuli, including cytokines and mitogens [4,5]. PG biosynthesis in the central nervous system and inflammatory cells is primarily attributed to COX-2, explaining in part the observed analgesic and anti-inflammatory properties of nonsteroidal anti-inflammatory drugs (NSAIDs) that inhibit COX-2 [2,6-9].

In addition to expressional variation, the differences in PG production have been attributed to the segregation of COX isozymes into divergent signaling pathways, which are supplied by separate substrate pools [10]. Distinct substrate pools are generated by coupling each COX isoform to specific phospholipases (for AA release), or by producing isoform-selective substrates. In the parent Applications, two neutral AA derivatives, anandamide (AEA) and 2-arachidonlyglycerol (2-AG), were shown to be COX-2-selective substrates and to be metabolized into PG ethanolamides and glyceryl esters, respectively [11,12] (FIG. 1). The basis for 2-AG selectivity was found to be dependent upon the same structural elements that provide for the selectivity of COX-2 inhibitors, mainly the COX-2 side pocket [2,13]. AEA and 2-AG are endogenous ligands for the cannabinoid receptors, and exhibit analgesic and anti-inflammatory properties in experimental models of pain and inflammation [14]. Drugs that inhibit endocannabinoid reuptake or degradation may be useful for the treatment of pain [15].

Thus, the present invention may be used to provide a system for distinguishing between COX-2 activity and COX-1 activity. In embodiments of the present invention, systems and methods are disclosed to exploit a COX-2 selective enzymatic reaction with lipoamino acids such as NAGly for specifically detecting and measuring COX-2 enzymatic activity.

In other embodiments of the present invention, COX-2 enzymatic activity is detected or measured by detecting or measuring novel $PGH_2$ metabolites, including, but not limited to: $PGH_2$-EA, $PGB_2$-EA, $PGD_2$-EA, $PGE_2$-EA, $PGF_{2\alpha}$-EA, $TxB_2$-EA, 6-keto-$PGF_{1\alpha}$-EA, 15-keto-PGE2-EA, 13,14-dihydro-15-keto-$PGE_2$-EA, $PGG_2$-EA, $PGH_2$-EA, $PGA_2$-EA, $PGJ_2$-EA, $PGJ_2$-EA derivatives, bicyclo-$PGE_2$-EA, $TxA_2$-EA and $PGI_2$-EA.

In certain embodiments, the COX-2 specific enzymatic activity is compared to COX-1 activity, for example, a COX-2/COX-1 ratio may be analyzed.

In certain embodiments of the present invention, the inventors provide standards for determining a relative or absolute measurement of COX-2 activity by comparison to a standard or a standard curve generated using the standard. For example, a standard can be used to generate a standard curve for normalization of particular test results.

In certain embodiments, a determination of the amount of COX-2 activity, by the measurement of $PGH_2$-EA, or $PGH_2$-Gly metabolites, is used to detect inflammation or cancer. In certain embodiments, a relative or absolute determination of inflammation or cancer in the subject is made.

In preferred embodiments of the present invention, the inventors have discovered that other AA derivatives, such as N-arachidonylglycine (NAGly), N-arachidonyl-alanine and δ-arachidonyl aminobutuyic acid induce analgesia in mice and suppresses formalin-induced tonic inflammatory pain in rats ([16,17]. NAGly is structurally analogous to AEA, but lacks affinity for the cannabinoid CB1 receptor [18] (FIG. 1). NAGly and its downstream metabolites are naturally present at significant levels in many of the same mammalian tissues that express COX-2 including the brain, spinal cord, and kidney [17]. These observations combined with the structural similarity of NAGly to other COX-2 substrates, prompted us to investigate the ability of COX-2 to utilize NAGly as a substrate. Additionally, the present inventors have discovered NAGly as the first selective substrate for COX-2 that bears a charge. The products of NAGly oxygenation are $PGH_2$-glycine ($PGH_2$-Gly) and hydroxyeicosatetraenoic glycine (HETE-Gly), together representing the first members of a novel class of amino acid eicosanoids. Site-directed mutagenesis indicates that Arg-513 is a critical determinant of COX-2-selective oxygenation of NAGly. These results enable the development of a model for NAGly binding in the active site of COX-2, that explains in part the isoform selectivity of NAGly oxygenation. Taken together, these results suggest that COX-2 directly regulates endogenous NAGly levels, while potentially producing a class of new lipid signaling molecules.

More specifically, an embodiment of the present invention is a method of detecting an activity of a COX-2 enzyme in a subject that comprises obtaining a sample of the subject; and detecting an amino acid eicosanoid metabolite in the sample. In this embodiment, the presence of the amino acid eicosanoid metabolite indicates the activity of the COX-2 enzyme of the subject.

Another embodiment of the present invention is a method of detecting an activity of a COX-2 enzyme in a subject that comprises obtaining a first sample of the subject; detecting a first level of an lipid mediator substrate; administering a COX-2 inhibitor; allowing a period of time to pass; obtaining a second sample of the subject detecting a second level of an lipid mediator substrate; and comparing the first level of the lipid mediator substrate with the second level.

Another embodiment of the present invention is a method for screening for a tumor or inflammation in a subject in need thereof that comprises obtaining a sample in a subject; measuring the amount of $PGH_2$-Gly or HETEGly metabolite in the sample; and relating the amount measured to an existence of a tumor or inflamation in a subject.

Yet another embodiment of the present invention is a method of detecting an activity of COX-2 in a subject that comprises obtaining a sample of the subject; and detecting a COX-2 specific metabolite of an lipoamino acid in the sample, wherein the presence of the COX-2 specific metabolite in the sample indicates the activity of COX-2 in the subject.

Finally, another embodiment of the present invention is a method of detecting an activity of COX-2 in a subject that comprises obtaining a sample of the subject; detecting a level of a lipid mediator substrate. In this embodiment, the level of the lipid mediator substrate is indicative of the COX-2 activity. Optionally, this embodiment may further include at least one of the following steps: administering a COX-2 inhibitor; allowing a period of time to pass; obtaining a second sample of the subject; detecting a second level of a lipid mediator substrate; and comparing the first measured level of the lipid mediator substrate with the second measured level of the lipid mediator substrate to detect the COX-2 activity in the subject.

DETAILED DESCRIPTION OF THE INVENTION

Figure 1:
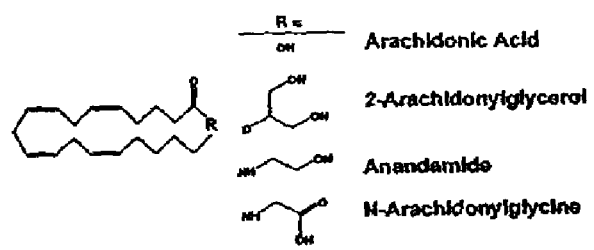
FIG. 1 shows the structure of various COX-2 Substrate Structures.

The present invention provides novel compositions, methods and articles of manufacture for detecting and measuring cyclooxygenase-2 (COX-2) activity in a subject or a sample thereof. Certain aspects of the present invention focus on detecting and measuring metabolites of AEA, such as, but not limited to, $PGE_2$-EA, $PGD_2$-EA and $TxA_2$-EA, and preferably metabolites of lipoamino acids such as, but not limited to $PGH_2$-glycine and HETE-Gly. The present invention provides novel compositions, methods and kits for detecting and measuring COX-2 activity, methods for identifying tumors in a subject, evaluating relative tumor severity, and following tumor response to therapy, and methods for detecting inflammation in a subject and evaluating relative inflammation severity. No aspect, embodiment or element, including the claims, of the present invention is bound by theory or mechanism.

In case of conflict, the present document, including definitions, will control. Unless otherwise indicated, materials, methods and examples described herein are illustrative only and not intended to be limiting. Of course, the terms used herein are readily understood by one of ordinary skill in the art.

Below are examples of definitions used herein and in the parent cases:

The term in vivo includes the meaning of processes occurring in an animal, in tissue or cell culture, or in samples taken from an animal or culture.

The term in vitro includes the meaning of processes occurring in systems wholly or partially purified from the natural environment, such as with purified enzymes or defined enzyme systems.

Purified means partially or wholly isolated away from the natural milieu of factors normally associated with a particular macromolecular species. In certain embodiments, the purified factor comprises 50 percent or more (on a molar basis) of all macromolecular species present in the isolated form. In certain embodiments, a purified composition will comprise more than about 80 percent of all macromolecular species present. In certain preferred embodiments, a purified composition comprises more than about 90 percent of all macromolecular species present. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species. In non-liquid compositions, "purified" is based upon dry weight and the same percent purities stated above are embodied.

A COX-2 selective substrate is a substrate that is transformed to an enzymatic reaction product by the COX-2 enzyme; but is not transformed, or is not significantly transformed, to a reaction product by the COX-1 enzyme. It is most preferred that a COX-2 selective substrate of the present invention is not enzymatically transformed to a reaction product by COX-1. In certain embodiments, COX-1 may have some activity on the COX-2 selective substrate, but it is not significant relative to the COX-2 activity. Relatively insignificant activity can be determined, for example, by measuring the ratio of substrate oxygenation using purified COX-1 and COX-2.

In certain embodiments, the ratio of COX-1 activity versus COX-2 activity for a COX-2 selective substrate, expressed as a percentage, is about 50% or less; in certain embodiments, 40% or less; in certain embodiments, 30% or less; in certain embodiments, 25% or less; in certain embodiments, 20% or less; in certain embodiments, 10% or less; in certain embodiments, 5% or less; in certain embodiments, 3% or less; in certain embodiments, 2% or less; and in certain preferred embodiments 1% or less. The lower the percentage (above), the more preferred the embodiment. A highly preferred COX-2 selective substrate is metabolized by COX-2, but is not metabolized by COX-1.

The terms "COX-2 specific substrate" and "COX-2 selective substrate" are used interchangeably herein.

In general, enzyme activity refers to the rate at which substrate is consumed or product is formed in an enzymatic reaction under a given set of reaction conditions. The Standard International (SI) unit for enzyme activity is an enzyme unit (U) and is defined as the amount of enzyme needed to produce 1 μmole product/minute. A unit may be defined differently herein (e.g., the amount of enzyme needed to produce 1 μmoles product per minute or the amount of enzyme needed to consume 1 μmole substrate per minute). Additional determinations of enzyme activity can be compared when utilizing similar or preferably identical reaction conditions. It is understood that reaction conditions can be changed and a new enzyme activity scale determined (e.g., by generating a standard curve of enzyme activity and use thereof, a process which is known to one of ordinary skill in the art). The specific activity of a particular enzyme preparation refers to the total enzyme units divided by the total amount of protein present in the preparation. A preferred unit of specific activity is U per mg of protein (U/mg).

As used herein, references to COX include both COX-1 and COX-2.

Arachidonyl ethanolamide (AEA) is defined herein to be a COX-2 selective substrate.

The terms "arachidonyl ethanolamide" and "anandamide" are used interchangeably herein.

As used herein, "prostaglandin ethanolamides" (PG-EAs) are included in the meaning of COX-2 selective metabolites.

Certain abbreviations include: cyclooxygenase (COX), cyclooxygenase-1 (COX-1), cyclooxygenase-2 (COX-2), prostaglandin (PG), prostaglandins (PGs), ethanolamide (EA), prostaglandin ethanolamides (PG-EAs), arachidonyl ethanolamide (AEA), prostaglandin-ethanolamide (PG-EA), thromboxane (Tx).

As defined herein and using the abbreviations above, PG-EAs can include, but are not limited to: $PGB_2$-EA, PGD2-EA, $PGE_2$-EA, $PGF_2\alpha$-EA, $TxB_2$EA, 6-keto-$PGF_1\alpha$-EA, 15-keto-PGE2-EA, 13,14-dihydro-15-keto-$PGE_2$-EA, $PGG_2$-EA, $PGH_2$-EA, $PGA_2$-EA, $PGJ_2$-EA, $PGJ_2$-EA derivatives, bicyclo-PGE2-EA, $TxA_2$-EA and $PGI_2$-EA (also referred to herein as prostacyclin-EA).

Tumor type typically references the tissue of tumor origin, but can also refer to the current tissue in which a tumor is located (e.g., colon cancer, liver cancer, or pancreatic cancer). The stage and grade of a tumor is related to severity and medical definitions of stages and grades within a continuum are known in the art for each tumor or cancer type. Each specialty within oncology (e.g., hematology, colorectal, liver, pancreatic, lung, brain, dermatology, etc.) may have a particular standard for the stage and grade scale of the tumors used within that clinical specialty, known to one of skill in that art, which varies from the general definitions of tumor stage and grade provided below.

Tumor grade is determined by the appearance of the tumor under the microscope and how quickly the tumor is likely to grow and spread. In general, grading systems are different for each type of cancer, but are known to one of ordinary skill in the art. For example, grade I tumors are the least malignant appearing, grade II tumors are moderately differentiated with a moderately malignant appearance, grade III tumors are less differentiated and show enhanced signs of tissue invasion, and grade IV tumors display the least differentiation and are the most malignant appearing. The grade of a tumor is determined by one of ordinary skill in the art.

The stage of a tumor refers to the extent of a cancer, how advanced the tumor is in the patient (e.g., whether the disease has spread from the original site to other parts of the body). The stage of a tumor is generally determined by radiographic studies such as a computed tomography (CT) scan, magnetic resonance (MRI) imaging and/or ultrasound. Tumor staging is determined by one of ordinary skill in the art and can vary by tumor type or as a field advances, standard staging practices may change. Certain definitions of stages for various cancers are provided in the Dictionary of Cancer Terms on CANCERNET which is a service of the National Cancer Institute available on the World Wide Web at "http://cancernet.nci.nih.gov/dictionary/dictionary-full.html", incorporated herein by reference in its entirety. A physical location for inquiry or obtaining a copy of the Dictionary of Cancer Terms is: NCI Public Inquiries Office; Building 31, Room 10A03; 31 Center Drive, MSC 2580; Bethesda, Md. 20892-2580.

Staging refers to performing exams and tests to learn the extent of the cancer within the body, especially whether the disease has spread from the original site to other parts of the body.

Cyclooxygenases and Prostaglandins

Prostaglandins produced as a result of the activity of COX are known to have numerous physiological functions. These functions include the antithrombogenic action of prostacyclin released by the vascular endothelium and the cytoprotective effect of prostaglandins produced by the gastric mucosa (Whittle, et al. 1980, *Nature*, 284:271-273). COX-2 is typically expressed following the activation of normal cells and certain a typically proliferating cells, by various pro-inflammatory agents including certain cytokines (Hla, T. and Nielson, K. 1992, *Proc. Natl. Acad. Sci. USA*, 89:7384-7388; Feng, et al. 1993, *Arch. Biochem. Biophys.*, 307:361-368), endotoxin (Lee, et al. 1992, *J. Biol. Chem.*, 267:25934-25938) and certain mitogens (Kujubu, et al. 1991, *J. Biol. Chem.*, 266:12866-12872; O'Banion, et al. 1991, *J. Biol. Chem.*, 266:23261-23267; and Hla, T. and Nielson, K. 1992, *Proc. Natl. Acad. Sci. USA*, 89:7384-7388).

Prostaglandins represent a class of substances produced in a wide variety of cells. In general, PGs act on the cells that produce them, on neighboring cells, or over short distances and can be classified as autocrine hormones. PGs and their relatives are usually thought of as potent local hormones (autocrine and paracrine) acting over a short lifetime. PGs, and related compounds, prostacyclin ($PGI_2$), thromboxanes (TX), leukotrienes (LT), and lipoxins (LP), derive from fatty acids stored in cellular membranes as phospholipids or triglycerides, especially arachidonic acid, with an open chain, 20-carbon structure. Prostaglandins generally resemble hairpins structurally with a five-membered ring and two chains extending from the ring. In general, substituents on the five-membered ring determine the subclass and activity of the prostaglandins. A series of synthetic reactions catalyzed by enzymes in the membranes, and certain non-enzymatic transformations, culminate in the release of prostaglandin product.

Detecting COX-2 Activity

As stated above, and in the parent application, AEA is an unique substrate specific for COX-2. COX-2 catalyzes the conversion of AEA to prostaglandin H2 ethanolamide ($PGH_2$-EA). The $PGH_2$-EA is subsequently enzymatically and nonenzymatically metabolized to a variety of compounds, such prostaglandin E2 ethanolamide ($PGE_2$-EA) and prostaglandin $D_2$ ethanolamide ($PGD_2$-EA). These downstream metabolites will be referred to, herein, as $PGH_2$-EA metabolites. $PGH_2$-EA metabolites include, but are not limited to, PGB2-EA, $PGD_2$-EA, $PGE_2$-EA, $PGF_2\alpha$-EA, $TxB_2$-EA, 6-keto-$PGF_1\alpha$-EA, 15-keto-PGE2-EA, 13,14-dihydro-15-keto-PGE2-EA, $PGG_2$-EA, $PGH_2$-EA, $PGA_2$-EA, $PGJ_2$-EA, $PGJ_2$-EA derivatives, bicyclo-$PGE_2$-EA, HETEs, $TxA_2$-EA and $PGI_2$-EA., which are metabolized directly from AEA by COX-2, will also be referred to as $PGH_2$-EA metabolites in this application.

In general, all prostaglandin and thromboxane ethanolamides are susceptible to enzymatic oxidation of the ethanolamide moiety and can undergo oxidation. The amount of $PGH_2$-EA metabolites in a biological sample correlates with the COX-2 specific activity in the subject from which the sample was collected. The amount of COX-2 activity is a marker of or a measurement of inflammatory or cancerous disease processes. Certain embodiments of the present invention include methods and materials for making sensitive measurements of picogram quantities of $PGH_2$-EA metabolites. Further embodiments of the present invention include using these measurements of COX-2 activity to clinically grade or stage a disease process and to assess therapeutic outcomes.

Additionally, as a preferred embodiment of the present invention, a lipoamino acid is the substrate for COX-2. Preferably, the lipoamino acid is NAGly, which COX-2 catalyzes into $PGH_2$-Gly and HETE-Gly.

Measuring Prostaglandin Ethanolamides

For the purposes of this application, detecting includes determining if a substance or compound is present in a sample. In the present invention, the substance or compound being detected is preferably a $PGH_2$-Gly or HETE-Gly metabolite. Detecting can include measuring. In general, measuring means determining the relative or absolute amount of a substance or compound detected. Measurement is generally, but not always, performed relative to a standard. For example, the amount of the standard may be correlated with an amount of COX-2 activity or expression. Therefore, comparing the amount of metabolites measured in a sample from a subject indicates an amount of COX-2 activity or expression in the subject.

The metabolites may be detected and measured in a variety of ways, examples of which are discussed in greater detail below. In certain embodiments of the present invention, for example, a sample is collected from a subject, and a selective COX-2 substrate of the present invention, such as NAGly, is added. Then, a corresponding metabolite is measured. In other embodiments, downstream metabolites may be measured.

In another embodiment of the present invention, for example, both a COX-1 substrate (such as arachidonic acid) and a COX-2 selective substrate (such as NAGly) are added to the sample. Then the amount of downstream metabolites derived from the enzymatic actions of COX-1 and COX-2 on each substrate are measured and compared. In both examples, the samples can be incubated with the substrates over time and a series of measurements of metabolites taken and compared in relation to the amount of time that passed.

Samples from the subject can be processed is several ways. For example, the sample may be extracted at least one time with a solvent, to remove the metabolites from the sample for analysis. Extraction can be followed by evaporation. The resulting residue may be redissolved in another solvent and analyzed. This process might involve several rounds of the extraction, evaporation and redissolving steps. Alternatively, the solution resulting from one or more extractions of the sample may be filtered and analyzed. In certain preferred embodiments, the sample is extracted, filtered and analyzed for metabolite content.

One aspect of the present invention is a method of detecting COX-2 activity in a biological sample, comprising: incubation of the biological sample with NAGly, extracting the sample with a solvent, evaporating the solvent to leave a residue and analyzing the residue for metabolites wherein the presence of metabolites is indicative of COX-2 activity. In certain embodiments, the amount of metabolites is measured and related to the quantity of COX-2, COX2 expression, or COX-2 activity. In general, the analysis of metabolites includes, but is not limited to, detection by liquid chromatography mass spectrometry.

Detection and Measuring Device

In general, a detection device for detecting PG metabolites of the present invention includes, but is not limited to, a mass spectrometer, a chromatography-coupled mass spectrometer, an immunoassay or an enzyme-linked immunoassay, or other means for detecting metabolites known in the art. For example, in certain embodiments of the present invention, liquid chromatography/mass spectrometry (LC/MS) is conducted, preferably with a Waters 2690 Separations Module with a Zorbax RX—C18 narrow bore column (15 cm×2.1 mm, 5 µm) interfaced to a Finnigan TSQ-7000 triple quadrupole mass spectrometer. Sodiated analytes are eluted with increasing concentrations of MeCN in 0.001% aqueous sodium acetate. Evaluation of PG metabolites in biological samples may be conducted with selected ion monitoring and quantification.

Separation Device

A variety of separation devices known in the art for separating prostaglandins from a sample may be used. In general, separation devices include, but are not limited to, extraction columns, affinity columns, filters, thin-layer chromatography plates and gels.

In certain embodiments of the present invention, a $PGH_2$-EA metabolite in a sample may be isolated or purified (separated partially or substantially from the natural constituents of a metabolite containing sample) using one or more techniques known in the art for the separation of chemical and especially prostaglandin compounds, for example, but not limited, to liquid chromatography.

Subjects

In certain embodiments of the present invention, the subject includes a mammal, such as a rodent, preferably a human, or a cultured cell of a mammal, including a cultured cell of a human. Other subjects include farm animals and show animals (horses, cattle, sheep, pigs and swine, goats, fowl, and the like), pets (dogs, cats, parrots, canaries and the like), animals kept in zoos and endangered species (elephants, lions, tigers, antelope, zebra, anteaters, water buffalo, pandas, cheetahs, kangaroos, ostriches, eagles, condors, finches, and the like) or a cultured cell of said animal.

Samples

In certain embodiments, the sample is urine or may be collected from or processed from urine. PG metabolites can be measured in urine by isotope dilution mass spectrometry.

The PG metabolites are generally stable in cell culture, bovine, canine and human CSF and human and rat plasma incubated about 5 hours at about 37° C.

In certain embodiments of the present invention, a plurality of samples may be collected from the subject, with a period of time being allowed to pass between consecutive collections of the samples. The amounts of $PGH_2$-EA metabolites present in these samples are measured, compared and related to the periods of time that had been allowed to passed between collections. In certain embodiments, the subject is a patient and the samples are taken in order to evaluate the effectiveness of anti-cancer therapy and to evaluate tumor state, severity or load in the patient.

In general, samples can be collected from or prepared from cultured cells. A variety of cells lines known to one skilled in the art are acceptable. In addition, primary cell cultures can be used. Methods for collecting and culturing primary cell cultures are well known in the art.

Antibody Synthesis

Monoclonal and polyclonal antibodies to $PGH_2$-EA metabolites or their metabolites can be made using standard antibody generation techniques in light of the present invention (Cohen, et al., U.S. Pat. Ser. No. 5,589,575, herein incorporated by reference; McCafferty, et al. 1996, *Antibody Engineering, a Practical Approach*, IRL Press; Mernaugh & Mernaugh 1994, *Methods for the Production of Monoclonal Antibodies*, in Molecular Methods in Plant Pathology). For example, monoclonal antibodies against $PGE_2$ are commercially available from Cayman Chemical (118 E. Ellsworth Rd., Ann Arbor, Mich. 48108, 800-364-9897) and chemiluminescent ELISA kits for several PGs, HETE and TxB2 are available from Assay Designs, Inc. (800 Technology Dr., Ann Arbor, Mich. 48108; 734-668-6113).

COX-2 and Inflammatory Diseases/Disorders

A wide variety of human diseases are associated with inflammation. These range from acute appendicitis to asthma, myocardial infarction, specific immunological disease processes, infection with viruses or bacteria, malignancy and metastasis, endotoxemia and reperfusion injury. Since COX-2 activity is important in the progression of these diseases, the present invention is a useful method of diagnosing or monitoring disease state. The present invention is also useful in detecting and treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, acquired immune deficiency syndrome, septic shock and other types of acute inflammation, and lipid histiocytosis. Essentially, the present invention can be used to facilitate the detection, measurement and treatment of any disorder which is etiologically linked to the inflammatory process.

For example, in certain aspects of the present invention, a sample is collected from a patient suspected of having an inflammatory disease or diagnosed with an inflammatory disease and a metabolite of NAGly in the sample is detected and measured. The amount of the metabolite present in the sample correlates with COX-2 activity in the patient and is a marker of the progress or severity of that disease or disease process. In another example, a series of samples are collected from the patient over a period of time. During that period of time, the patient undergoes treatment for the inflammatory disease. Changes in the amount of metabolite measured over time are indicative of changes in COX-2 activity and changes in the patients disease state. This information would be used by the physician to evaluate the patient's condition as well as the effectiveness of therapeutic intervention, wherein a decrease in the metabolites or COX-2 activity is indicative of an improvement in the patient's condition or effective therapy.

COX-2 and Cancer

Studies in human colon cancer have shown that COX-2 expression is increased in colon cancer cells compared to the adjacent colonic mucosa; similar observations have been made in experimental models of colon cancer (Eberhart, C E, et al. 1994, *Gastroenterology* 107:1183; Sheng, H, et al. 1997, *J. Clin. Invest* 99:2254; DuBois, R N, et al. 1996, *Gastroenterology* 110:1259). COX-2 expression is a marker for the metastatic potential of colon cancer cells and is related to patient survival (Tsujii, M, et al. 1997, *Proc. Natl. Acad. Sci. USA* 94:3336; Sheehan, K M, et al. 1999, JAMA 282:1254). In one study, for example, COX-2 expression was determined in 76 patients with a variety of stages of colorectal cancer (Sheehan, K M, et al., 1999, *JAMA* 282: 1254). Such studies can be used to generate a standard curve for COX-2 expression in cancer and colon cancer in particular (see supra). Ten-year survival was significantly higher in patients with the lowest levels of COX-2 expression (68 versus 35 percent). These findings suggest that COX-2 activation promotes tumor growth. Consistent with this hypothesis is a study in which human colon cancer cells that expressed high levels of COX-2 were implanted into nude mice. Treatment with a selective COX-2 inhibitor reduced tumor formation by 85 to 90 percent and inhibited colony formation of cultured cells (Sheng, H, et al. 1997, *J. Clin. Invest* 99:2254). This benefit was not seen with tumor cells that lacked COX-2.

Certain aspects of the present invention include methods of detecting a tumor in a patient in need thereof, comprising: obtaining a sample of the patient and detecting at least one metabolite of the present invention in the sample. The presence of the metabolite in the sample is a marker for the presence of the tumor in the patient. More preferably, an amount of metabolite detected in the sample of the patient will be measured, wherein the amount of metabolite measured is indicative of the amount or severity of tumor present in the patient.

A further aspect of the present invention is a method of measuring and monitoring the size, grade, and/or stage of a tumor, comprising: collecting a first sample of a subject and measuring the amount of metabolites of the present invention in the first sample. Then a period of time is allowed to pass, during which the subject may, or may not, undergo anti-cancer therapy. After the period of time has passed, a second sample is collected from the subject and the amount of metabolites in the second sample is measured. The amounts of the metabolites in the first and second samples are compared, wherein the difference between the amounts of metabolites in the two samples is indicative of changes in the metabolism of the cancer cell.

In certain embodiments of the present invention, a plurality of samples may be collected from the subject, with a period of time being allowed to pass between consecutive collections of the samples. The amounts of metabolites present in these samples are measured, compared and related to the periods of time that had been allowed to pass between collections. In certain embodiments, the subject is a patient and the samples are collected in order to evaluate the effectiveness of anti-cancer therapy and to evaluate tumor severity or tumor load in the patient.

In general, the effectiveness of the anti-cancer therapy is evaluated based on the changes in the amount of sample metabolite observed over time. For example, increases in the amount of metabolites over time indicate continued tumor growth and failure therapeutic intervention; whereas decreases in the amount of metabolites over time are indicative of therapeutic success and tumor regression. In certain embodiments of the present invention, the sample is a culture of cancer cells used as an experimental model or a culture of cancer cells taken from a patient. The cultured cancer cells may be treated with an anti-cancer therapy in vitro in order to evaluate the effectiveness of that therapy in relation to alternative cancer therapies. In certain embodiments, this procedure is done in order to determine an optimal anti-cancer therapy for that individual patient.

In certain embodiments, the attending health professional may characterize both an inflammatory process and a malignancy in the subject by detecting or measuring an amount of a prostaglandin ethanolamide in a sample of a subject specifically produced by the offending malignancy and inflammatory lesion.

COX-2 and Research

In the prior art, investigations which attempt to identify links between COX-2 expression/activity and disease processes are time- and labor-intensive and often require examination of tissue samples post-mortem. For example, attempts to study the role of COX-2 in Alzheimer's disease (AD) require postmortem collection of brain tissue from both deceased AD and control subjects and quantitative assessment of COX-2 expression in this tissue using standard biochemical techniques (e.g., Western blotting). Such studies are also hampered by the inability to assess enzyme activity, which may or may not correlate with enzyme expression. The use of PG metabolites quantification in this setting allows for a relatively non-invasive quantification of COX-2 activity in vivo. This technique provides at least two fundamental benefits. First, the noninvasive nature allows for much broader testing increasing the sample size in these studies and permitting rapid and statistically significant association (or lack thereof) between COX-2 activity and the pathology under study. Second, given the possibility of testing patients before disease signs are evident will allow for assessing the role of COX-2 in disease development and progression in contrast to post-mortem studies which evaluate the role of COX2 long after the disease process began. Quantification of PG metabolites of the present invention in vivo provides a simple assay for assessing the in vivo efficacy of newly developed COX-2 inhibitors.

Kits

Certain embodiments of the present invention provide an article of manufacture for the detection and/or measurement of COX-2 activity by the detection and/or measurement of PGH$_2$-EA or PGH$_2$-Gly metabolites by radioassay or immunoassay, comprising an antibody and a set of instructions delineating a process for relating a detection and/or measurement of PG metabolites in a sample to a detection and/or measurement of COX-2 in a subject or a sample thereof. Preferably, the article of manufacture further comprises an antibody against the metabolites. More preferably, the article of manufacture further comprises the standard reagents required to perform an immunoassay, such as buffers, multiwell plates, additional antibodies and the like. Still more preferably, the article of manufacture further comprises one or more solid phase extraction columns for the isolation/purification of the metabolites. Preferably, the article of manufacture further comprises a set of standards. More preferably, the article of manufacture further comprises an unlabeled PG metabolite internal standard for standard curve development.

In further embodiments the present invention provides an article of manufacture for the detection and/or measurement of COX-2 activity by mass spectrometry, which comprises: a set of instructions delineating a process for relating a detection and/or measurement of PG metabolites in a sample to a detection and/or measurement of COX-2 in a subject or a sample thereof and a C18 solid phase extraction column. Preferably, the article of manufacture further comprises a set of standards. More preferably, the article of manufacture further comprises an unlabeled PG metabolite positive control, and a tetradeutereated PG metabolite internal standard.

Accordingly, the present invention establishes a role for COX-2 in the metabolism and regulation of an anti-inflammatory lipoamino acid, such as NAGly, . COX-2 oxygenates NAGly with a moderate efficiency, in contrast to absence of metabolism by COX-1. Without being bound by theory, ranking the catalytic efficiency of COX-2 substrates from the most to the least efficient (AA>2-AG>NAGly>AEA), suggests that modification of the alcohol group in AEA to the carboxylic acid in NAGly, promotes higher affinity and more productive binding for catalysis by COX-2 [12,22]. Additionally, the products identified here from NAGly oxygenation are similar to those obtained from the COX-2 metabolism of other substrates [1,11,12]. These products represent enzymatically derived HETE-GA and PGH$_2$-GA which displays a characteristic 2 mass unit shift after endoperoxide reduction, to form the product PGF2a-GA. These results suggest a role for COX-2 in the regulation and formation of a novel class of eicosanoids from NAGly metabolism.

Figure 6:
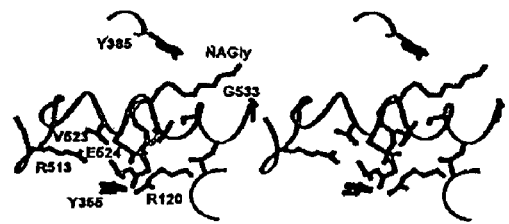
FIG. 6 shows a model of NAGly in the COX-2 active site. A stereo view of the predicted interactions between NAGly and the active site residues of mCOX-2.

Investigation of the NAGly/COX-2 interactions through site-directed mutagenesis indicate that three polar residues in the COX-2 active site, Arg-120, Arg-513, and Glu-524 contribute to the binding and oxygenation of NAGly. These studies further suggest that the side pocket residues, primarily Arg-513, are critical determinants of the COX-2 selective oxygenation of NAGly. These findings agree with previous mutagenesis studies involving the selective COX-2 substrate, 2-AG [13]. Directed by the results of these mutagenesis studies, a model for the binding of NAGly to the active site of COX-2, discussed in the Examples below, was developed using geometry optimization and molecular dynamics simulation, as outlined in Materials and Methods (FIG. 6). The examples resulted in the formation of an ionic bond between the NAGly carboxylate and the guanidinium ion of Arg-513. The guanidinium ion of Arg120 moved to ion pair with the carboxylate of Glu-524, similar to the conformation observed in the crystal structure of a zomepirac derivative bound to COX-2 [28]. The amide carbonyl of NAGly was positioned within hydrogen bonding distance to the secondary amide of Arg-120. This suggests the formation of a complex network of ionic and hydrogen bonds, between the glycine moiety of NAGly and the three residues of COX-2 involved in NAGly oxygenation (FIG. 6).

These results demonstrate that the COX-2 active site can accommodate a lipoamino acid in a productive conformation similar to those of other substrates, and upon oxygenation leads to the formation of a novel class of eicosanoids. In contrast to the neutral endocannabinoids 2-AG and AEA, NAGly is the first charged COX-2 selective substrate identified [11,12] (FIG. 1). The highest levels of NAGly are observed in tissues that can be induced to express COX-2 [17]. NAGly metabolism by COX-2 may represent a mechanism for inactivation of this anti-inflammatory lipoamino acid, similar to the role of fatty acid amide hydrolase [17]. Coincidentally, the anti-inflammatory and analgesic properties of NAGly are similar to many NSAIDs that would inhibit the COX-2 metabolism of NAGly [2,6-9,16,17]. It is possible that COX-2 inhibition reduces pro-inflammatory PG production, and effectively raises the levels of anti-inflammatory lipid mediators such as NAGly and the endocannabinoids.

EXAMPLES

The following Examples are set forth to provide specific examples of the present invention, and are not intended to limit the scope of the present invention in any way. Furthermore, one of ordinary skill in the art would understand that certain examples below can be modified as appropriate to detect levels of a PGH$_2$-Gly metabolite where examples of a PGH$_2$-EA metabolite are disclosed below.

Example 1

A sample may be urine or may be collected from or processed from urine. PGH$_2$-Gly metabolites can be measured in urine by isotope dilution mass spectrometry. A fixed volume of urine is treated with an appropriate internal standard and then loaded on reversed-phase extraction cartridges. The sample is then washed (e.g., 1 ml pH 4.0 20 mM Sodium acetate) and PG metabolites including the added internal standard are eluted with organic solvent (e.g., two 1 ml aliquots of MeCN). The solvent is evaporated and the residue is analyzed by LC/MS.

Example 2

COX-2 expression and activity are generally linked with the inflammatory process, which accompanies a plethora of pathologies including, but not limited to, arthritis/arthropathy, infectious disease, neurodegenerative disease, neoplasia and autoimmune disease. The quantification of prostaglandin PGH$_2$-Gly metabolites from biological fluids obtained non-invasively (e.g., blood, urine) will allow for the assessment of COX-2 activity in vivo, reflecting both inflammation and disease severity. In addition, serial testing will allow for the tracking of the natural course of the disease as well as the efficacy of antiinflammatory therapy. A model for this application would be the ubiquitous use of C-reactive protein (CRP) in the diagnosis and assessment of diseases associated with inflammation. The benefits of using PGH$_2$-Gly metabolites in this context instead of more traditional diagnostic markers, such as CRP, involve the highly specific nature of PGH$_2$-Gly metabolite production. PGH$_2$-Gly metabolites are elevated only when COX-2 activity is elevated whereas CRP elevations, for example, are very non-specific.

Scenario: Elderly woman seeks medical attention for recent onset of joint pain in hands. Urine is collected and $PGH_2$-Gly metabolite quantification is conducted. $PGH_2$-Gly metabolites are elevated supporting a diagnosis of rheumatoid arthritis. COX-2 inhibitor therapy is initiated (e.g., celecoxib). After one week, symptoms are only mildly relieved and another urine sample reveals $PGH_2$-Gly metabolite levels are still elevated, indicating that the inflammatory process is still active. Following dosage increase, symptoms are relieved and urinary $PGH_2$-Gly metabolites are normalized.

Example 3

COX-2 expression and activity are linked to several solid tumors, most notably colorectal adenocarcinoma. The quantification of $PGH_2$-Gly metabolites from biological fluids, described herein, provide a noninvasive "early-warning" for clinically undetectable neoplasia. In addition, serial testing following diagnosis will allow for the tracking of the natural course of the cancer as well as the efficacy of antineoplastic therapy. A model for this application would be the use of prostate specific antigen (PSA) in the diagnosis and assessment of prostate adenocarcinomas. The benefits of $PGH_2$-Gly metabolite quantification in this context include (a) relative noninvasiveness, (b) sensitivity (most cancers are advanced once symptomatic) and (c) cost (simple lab diagnostic technique versus colonoscopy for example).

Scenario: Elderly asymptomatic man receives annual physical examination. Urine and blood are collected and $PGH_2$-Gly metabolite quantification is conducted. $PGH_2$-Gly metabolites are elevated in both the urine and plasma, prompting a more detailed search for possible neoplasia. Colonoscopy reveals a single polyp in the descending colon which, following biopsy, proves malignant. Standard chemotherapy is initiated. Following treatment, urinary and plasma $PGH_2$-Gly metabolite levels have normalized. Annual colonoscopies for 3 years reveal no recurrence. After 3½ years, patient visits physician for an unrelated reason and urinary $PGH_2$-Gly metabolites are quantified. $PGH_2$-Gly metabolite levels are markedly elevated, indicating the recurrence of carcinoma. The physician recommends colonoscopy, which reveals the presence of carcinoma. Aggressive chemotherapy is initiated and urinary $PGH_2$-Gly metabolite levels are monitored.

Example 4

The measurement of $PGH_2$-Gly metabolites from in vitro samples (e.g., cell culture, biopsy samples) allows for the direct quantification of COX-2 activity. Current methods which quantify cyclooxygenase activity do not directly distinguish between COX-1 and COX-2. Methods which quantify COX-2 expression (e.g., Western blotting) do not assess activity which may or may not correlate with expression levels.

Scenario: Researchers investigating new NSAIDS expose cultured cells expressing COX-2 to various concentrations of test compounds for predetermined periods of time. At the conclusion of the exposures, conditioned medium is collected from each culture. The samples of conditioned medium are assayed for the presence of $PGH_2$-Gly metabolite. The researchers find that most of the test compounds have no significant affect on the production of $PGH_2$-Gly metabolite by the cultured cells. However, one compound ("compound X") dramatically reduces the amount $PGH_2$-Gly metabolite produced by the cultured cells. Therefore, "compound X" inhibits COX-2. The researchers focus their efforts on "compound X," which may become a new COX-2 specific treatment of inflammatory diseases or cancer. In further experiments, the researchers determine that compound X does not inhibit COX-1. Compound X is, therefore, identified as a COX-2 specific inhibitor.

Example 5

In certain embodiments, the present invention can be employed to identify a previously undescribed small molecule modulator of COX-2 activity. This can be done with the following method. Briefly, RAW264.7 cells at 30-40% confluence are activated with lipopolysaccharide (LPS, 20 ng/mL) and treated with a series of concentrations of a test compound. Cells are incubated for 12 h at 37° C. and then medium is removed and replaced with buffered saline. Cells are then treated with 50 µM NAGly and incubated an additional 30 min at 37° C. Following incubation, buffered saline is collected and treated with tetradeutereated $PGH_2$-EA metabolite standard. Buffered saline is extracted twice with equal volumes of 2:1 $CHCl_3$:MeOH. The combined organic extract is evaporated under a stream of argon. The resultant residue is redissolved in 1:1$H_2O$:MeCN and analyzed by liquid chromatography-mass spectrometry (LC-MS) with selected ion monitoring of $PGH_2$-Gly metabolite peaks at m/z=418 and. Quantitation of COX-2 activity is accomplished by comparing the area of the $PGH_2$-Gly metabolite peak to that of the internal standard.

Example 6

This example compares steady-state kinetic parameters for COX-2 mediated oxygenation of AA and NAGly.

Materials and Methods

Chemicals: AA was obtained from NuChek Prep (Elysian, Minn.). N-Arachidonylglycine was purchased from Cayman Chemical (Ann Arbor, Mich.). Ram seminal vesicles were obtained from Oxford Biomedical Research (Oxford, Mich.). Hematin and triphenylphosphine were purchased from Sigma. All other chemicals were from Aldrich.

Enzymology: COX-1 was purified from ram seminal vesicles as previously described [19]. Site-directed mutagenesis of COX-2 was performed as described previously [20]. Recombinant COX-2 enzymes were expressed in Sf-9 insect cells and purified by ion-exchange chromatography and gel filtration as previously described [20]. Apoenzymes were reconstituted with hematin prior to activity assays.

Steady-state kinetic experiments were performed in 100 mM Tris-HCl buffer containing 500 µM phenol, by incubating 50 nM COX-2 with AA (1.5 50 µM) or NAGly (1.5-150 µM) in a Gilson Model 5/6 oxygraph (Gilson Medical Electronics, Inc., Middletown, Wis.) fitted with a Clark electrode and a thermostatted cuvette. COX activity was quantified as previously described [21]. Initial reaction velocity data were obtained from the linear portion of the oxygen uptake curves. Oxygraph data were analyzed by nonlinear regression with Enzyme Kinetics 1.5 software (Trinity Software, Campton, N.H.).

Mass Spectrometry: Reactions for product characterization by mass spectrometry (MS) were performed in 100 mM Tris-HCl buffer containing 500 µM phenol, by incubating 86 µg COX-2 with 20 µg of NAGly for 2 min at 37° C.

Reactions were quenched with 3 volumes of ice-cold methanol with or without triphenylphosphine (1 mg/ml). Samples were centrifuged at 14,000 rpms for 10 min at 4° C. Aliquots were removed and dried to completeness under a stream of argon. Samples were prepared for mass spectral analysis by reconstitution in 0.2% aqueous acetic acid solution and purification on a Waters Oasis HLB solid phase extraction cartridge. The samples were eluted from the cartridge with 100% methanol and diluted in acetonitrile:water:triethylamine (1:1:0.001) prior to analysis. Mass spectral analysis was performed by directly infusing the diluted samples (flow rate=10 B1/min) into a Finnigan TSQ 7000 triple quadrupole mass spectrometer equipped with an electrospray ionization source and operated in the negative ion mode. The TSQ 7000 was set to the following parameters: Capillary Voltage=−15.0 V; Tube Lens Voltage=−60.0 V; Spray Voltage=3.5 kV; Sheath Gas=60 psi; Auxiliary Gas=10 (no units).

Energy Minimization and Modeling: NAGly was built into the protein coordinates of uninhibited COX-2 (Protein Data Bank code 5COX). All amino acid positions were fixed except for the side chains of Arg-120, Arg-513, Glu524, and Tyr-355. The carboxylic acid of NAGly was restrained within 3.6 Å from the hydrogen bond donor/acceptor groups of Arg-513 and Glu-524, while the amide carbonyl was restrained within 3.6 Å of Arg-120. The Tyr-385 hydroxyl group was restrained within 3.6A from NAGly carbon C13 to ensure a productive conformation for oxygenation. The complex was energy minimized for 1000 iterations using a conjugate gradient in the consistent valence forcefield. Molecular dynamic simulations were then run on the energy minimized assemblies for 1000 iterations at 300K. All simulations were performed using the Discover module of Insight II 2000 with a R12000 Silicon Graphics Octane workstation.

Results

Figure 2:
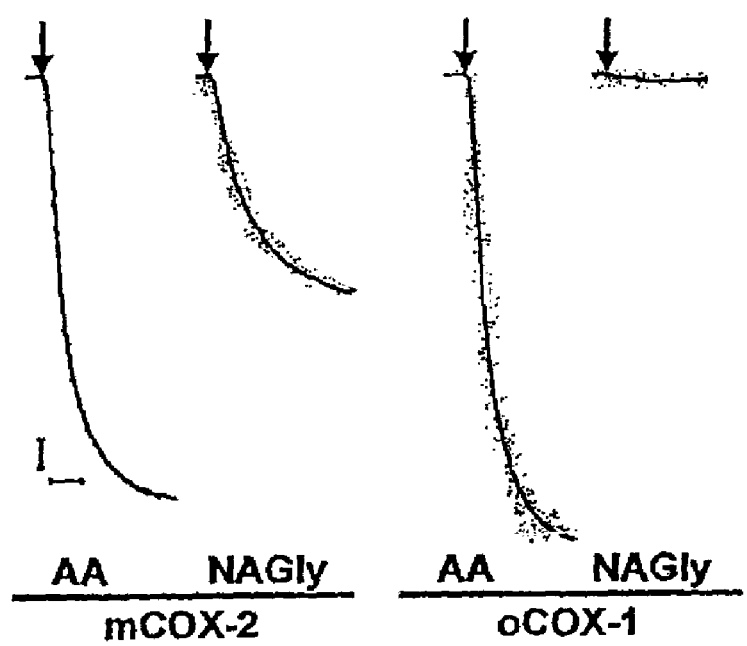
FIG. 2 shows oxygenation of NAGly by COX-2. Representative $O_2$ uptake curves for 200 μM NAGly or 100 μM AA treated with 200 nM purified mCOX-2 or 150 nM oCOX-1 (indicated by arrow) are shown. The horizontal bar represents 20 s; the vertical bar represents 5 μM $O_2$.

Oxygenation of NAGly by Purified COX-2: Incubation of NAGly with purified recombinant murine COX-2 (mCOX-2) gave 40% of the initial rate of $O_2$ uptake of that observed with AA (FIG. 2). Relatively little $O_2$ uptake if any, was observed after the addition of ovine COX-1 (oCOX-1) to the reaction containing NAGly. In contrast, COX-1 metabolizes AEA and 2-AG, but still to a much lesser extent than AA. These results show that NAGly is the most selective substrate identified to date. Steady-state kinetic analysis revealed that the $K_m$ for NAGly was 3.5-fold higher than the $K_m$ for AA, and the $k_{cat}/K_m$ for NAGly was almost 10-fold less than the kcat/Km for AA (Table I).

TABLE 1

Steady-state kinetic parameters for COX-2 mediatedoxygenation of AA and NAGly

|  | kcat s-1 | Km μM | kcat/Km s-1 μM-1 |
| --- | --- | --- | --- |
| Murine COX-2 |  |  |  |
| AA | 16.6 ± 1.7 | 3.3 ± 1.0 | 5.08 |
| NAGly | 6.3 ± 1.1 | 11.7 ± 1.4 | 0.54 |

Comparing kcat/Km values reported for the other selective substrates NAGly is 4-fold less efficient than 2-AG with a kcat/Km of 2.3 s-1 μM-1, but 8-fold more efficient than AEA with a kcat/Km of 0.065 s-1 μM-1 [12,22].

Figure 3:
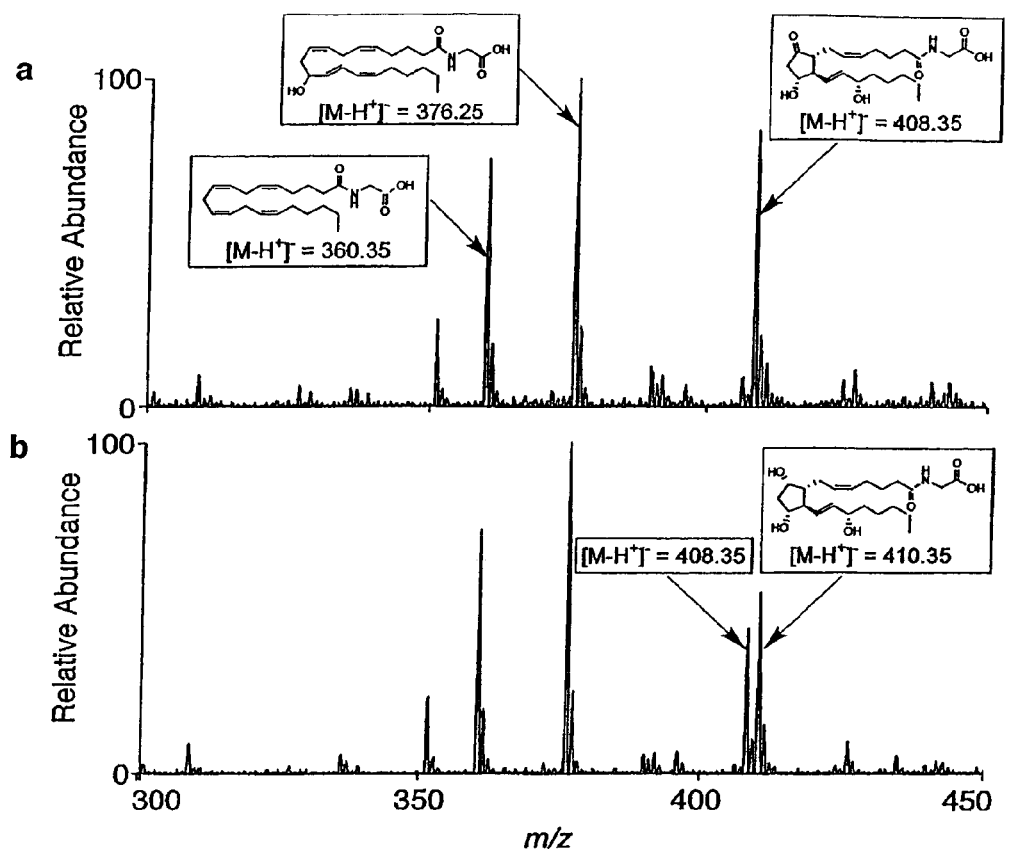
FIG. 3 shows mass spectrometry of oxygenated NAGly products. Representative direct liquid infusion, negative ion, electrospray ionization mass spectra of NAGly metabolites produced by incubating 20 μg of NAGly with 86 μg of purified holo-mCOX-2 (panel a) for 2 min at 37° C. or (panel b) for 2 min at 37° C. followed by reduction with triphenylphosphine. Chemical structures indicate possible assignments for the most abundant products with the appropriate mass-to-charge ratio.

Identification of Oxygenated NAGly Metabolites: The products of NAGly metabolism by purified mCOX-2 were identified using mass spectrometry. Resolubilized COX reaction mixtures were directly infused into a triple quadrupole mass spectrometer and analyzed following electrospray ionization. Three major peaks were observed at m/z ratios that correspond to the deprotonated NAGly (m/z=360), 11- or 15-HETE-Gly (m/z=376), and PGH2Gly, PGE2-Gly or PGD2-Gly (m/z=408) (FIG. 3a). Treatment of NAGly/mCOX-2 reaction mixtures with the endoperoxide reducing agent triphenylphosphine resulted in a reduction of the peak height at m/z 408, and the appearance of a product at m/z 410 (FIG. 3b). This 2 mass unit shift is consistent with endoperoxide reduction of $PGH_2$-Gly to form PGF2a-Gly.

Enzyme Structural Requirements for NAGly Oxygenation: The structural requirements for NAGly oxygenation were probed by site-directed mutagenesis of mCOX-2. The active site tyrosyl radical formed at Tyr-385 initiates substrate oxygenation by 13-pro-S hydrogen abstraction, and when mutated to Y385F fails to oxidize neither AA nor NAGly [2]. AA binds in the COX active site with the ¶-end near Gly-533 [20,27]. The G533V mutant was used to incorporate steric hindrance near the ¶-end of the substrate channel to test the L-shaped conformation of NAGly. As expected no $O_2$ uptake was observed after NAGly incubation with G533V. These results indicate that NAGly does bind in an L-shaped conformation, and requires Tyr-385 for catalysis.

Figure 4:
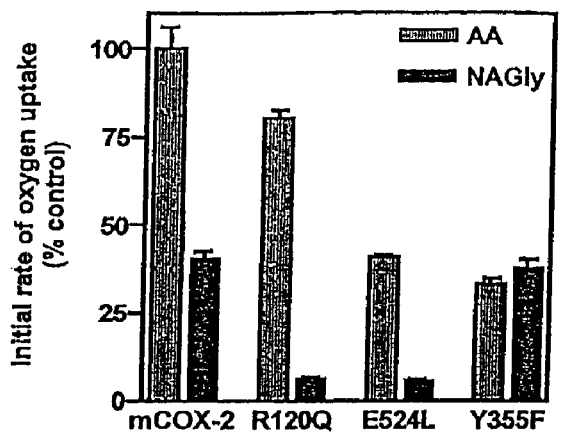
FIG. 4 shows oxygenation of AA and NAGly by constriction site mutants of COX-2. Initial $O_2$ uptake rates by wild-type and mutant mCOX-2 enzymes (200 nM) with AA (100 μM) and NAGly (200 μM) are shown, and are normalized to the initial rate of O2 uptake for AA with wild-type enzyme (mean±S.E., n=3).

At the bottom of the substrate (and inhibitor) binding site, there is a hydrogen bonding network comprised of residues Arg-120, Tyr-355, and Glu524, that form a constriction which is present in both COX isoforms. These residues contribute to the binding of the carboxylate in both AA and NSAIDs, and the glycerol moiety of 2-AG [12,23-27]. Site-directed mutants that reduce the hydrogen bonding capabilities of the constriction, such as R120Q, Y355F, and E524L, were used to probe interactions between NAGly and mCOX-2. These mutants displayed a modestly reduced capacity for AA oxygenation (<3-fold reductions) (FIG. 4). However, the R120Q and E524L mutants exhibited a 6- and 7-fold reduction in the initial rate of NAGly oxygenation, when compared with wild-type (FIG. 4). Interestingly, the Y355F mutant was more active towards NAGly, than AA (FIG. 4). These results suggest that Arg-120 and Glu-524 are critical for NAGly oxygenation, and Tyr-355 seems to be relatively uninvolved.

Figure 5:
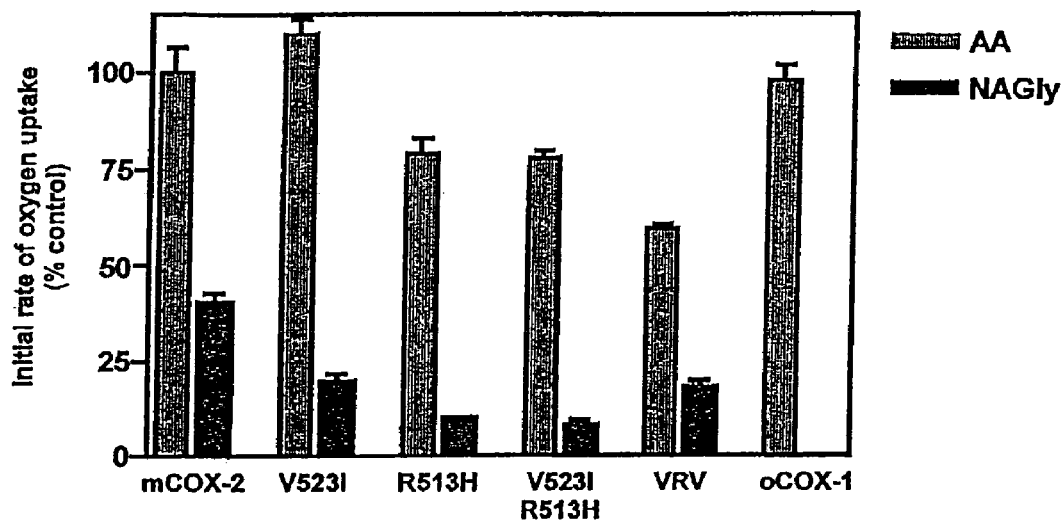
FIG. 5 shows oxygenation of AA and NAGly by side pocket mutants of COX-2. Initial $O_2$ uptake rates by wild-type and mutant mCOX-2 enzymes (200 nM) with AA (100 μM) and NAGly (200 μM) are shown, and are normalized to the initial rate of $O_2$ uptake for AA with wild-type enzyme (mean±S.E., n=3).

The side pocket of COX-2 is an extra solvent accessible space in the active site that contributes to the selectivity of inhibitors and substrates [2,12]. Previous studies have identified residues in the side pocket of COX-2, especially Arg-513, as critical determinants of 2-AG oxygenation by COX-2 [13]. Mutations that change COX-2 side pocket residues (Val-434, Arg-513, and Val-523) to their corresponding amino acids in COX-1 (Ile-434, His-513, and Ile-523), were tested for effects on NAGly oxygenation. As previously reported, the mutations did not greatly affect the COX-2 ability to metabolize AA [13] (FIG. 5). The V523I mutation modestly reduced the initial rate of NAGly metabolism to 50% of that observed with wild-type enzyme. The R513H mutation markedly reduced the NAGly oxygenation rate, and the double mutant R513H/V523I was indistinguishable from R513H alone (FIG. 5). All enzymes that contained histidine at position 513, including the triple mutant V4341/R513H/V523I (VRV) and oCOX-1, displayed a reduced ability to oxygenate NAGly (FIG. 5).

These results are similar to those obtained with 2-AG, and thus it appears that Arg-513 dictates in part, the isoform selectivity of the novel substrate NAGly [13].

REFERENCES

As stated above, all references, including U.S. Patents, non U.S. Patents, journal articles, and newspaper articles referred to herein are hereby made part of the specification of the present patent and incorporated herein in their entirety by reference. This includes, but is not limited to the below listed references.

The numbers before the references listed below correspond with the bracketed numbers throughout the Specification.

[1] Hamburg, M., and Samuelsson, B. (1973) Detection and isolation of an endoperoxide intermediate in prostaglandin biosynthesis. Proc Natl Acad Sci USA. 70, 899-903.

[2] Kurumbail, R. G., Kiefer, J. R., and Marnett, L. J. (2001) Cyclooxygenase enzymes: catalysis and inhibition. Curr. Opin. Struct. Biol. 11, 752-760.

[3] Smith, W. L., DeWitt, D. L., and Garavito, R. M. (2000) Cyclooxygenases: Structural, cellular, and molecular biology. Annu. Rev. Biochem. 69, 149-182.

[4] Evett, G. E., Xie, W., Chipman, J. G., Robertson, D. L., and Simmons, D. L. (1993) Arch. Biochem. Biophys. 306, 169-177

[5] Herschman, H. R. (1996) Biochim. Biophys. Acta. 1299,125-140

[6] Masferrer, J. L. (1994) Selective inhibition of inducible cyclooxygenase 2 in vivo is anti-inflammatory and non-ulcerogenic. Proc. Natl. Acad. Sci. USA. 91, 3228-3232.

[7] Vane, J. R., Mitchell, J. A., Appleton, I., Tomlinson, A., Bishop-Bailey, D., Croxtall, J., and Willoughby, D. A. (1994) Inducible isoforms of cyclooxygenase and nitric-oxide synthase in inflammation. Proc. Natl. Acad. Sci. USA. 91, 2046-2050.

[8] Kennedy, B. P., Chan, C. C., Culp, S. A., and Cromlish, W. A. (1993) Cloning and expression of rat prostaglandin endoperoxide synthase (cyclooxygenase)-2 cDNA. Biochem. Biophys. Res. Commun. 197, 494-500.

[9] Vane, J. R. (1971) Inhibition of prostaglandin synthesis as a mechanism of action for aspirin-like drugs. Nat. New Biol. 231, 237-239

[10] Smith, W. L., and Langenbach, R. (2001) Why there are two cyclooxygenaseisozymes. J. Clin. Invest. 107, 1491-1495.

[11] Yu, M., Ives, D., and Ramesha, C. S. (1997) Synthesis of prostaglandin E2 ethanolamide from anandamide by cyclooxygenase-2. J. Biol. Chem. 272, 21181-21186.

[12] Kozak, K. R., Rowlinson, S. W., and Marnett, L. J. (2000) Oxygenation of the endocannabinoid, 2-arachidonylglycerol, to glyceryl prostaglandins by cyclooxygenase-2. J. Biol. Chem. 275, 33744-33749.

[13] Kozak, K. R., Prusakiewicz, J. J., Rowlinson, S. W., Schneider, C., and Marnett L. J. (2001) Amino acid determinants in cyclooxygenase-2 oxygenation of the endocannabinoid 2-arachidonylglycerol. J. Biol. Chem. 276, 30072-30077.

[14] Pertwee, R. G. (2001) Cannabinoid receptors and pain. Prog. Neurobiol. 63, 569-611.

[15] Walker, J. M., Huang, S. M., Strangman, N. M., Tsou, K., and SanudoPena, M. C. (1999) Pain modulation by release of the endogenous cannabinoid anandamide. Proc. Natl. Acad. Sci. USA. 96, 12198-12203.

[16] Burstein, S. H., Rossetti, R. G., Yagen, B., and Zurier, R. B. (2000) Oxidative metabolism of anandamide. Prostaglandins Other Lipid Mediat. 61, 29-41

[17] Huang, S. M., Bisogno, T., Petros, T. J., Chang, S. Y., Zavitsanos, P. A., Zipkin, R. E., Sivakumar, R., Coop, A., Maeda, D. Y., De Petrocellis, L., Burstein, S. Di Marzo, V., and Walker, J. M. (2001) Identification of a new class of molecules, the arachidonyl amino acids, and characterization of one member that inhibits pain. J. Biol. Chem. 276, 42639-42644.

[18] Sheskin, T., Hanus, L., Slager, J., Vogel, Z., and Mechoulam, R. (1997) Structural requirements for binding of anandamide-type compounds to the brain cannabinoid receptor. J. Med. Chem. 40, 659-667.

[19] Marnett, L. J., Siedlik, P. H., Ochs, R. C., Pagels, W. R., Das, M., Honn, K. V., Warnock, R. H., Tainer, B. E., and Eling, T. E. (1984) Mechanism of the stimulation of prostaglandin H synthase and prostacyclin synthase by the antithromotic and antimetastatic agent, nfazatrom. Mol. Pharmacol. 26, 328-335.

[20] Rowlinson, S. W., Crews, B. C., Lanzo, C. A., and Marnett L. J. (1999) The binding of arachidonic acid in the cyclooxygenase active site of mouse prostaglandin endoperoxide synthase-2 (COX-2). A putative L-shaped binding conformation utilizing the top channel region. J. Biol. Chem. 274, 23305-23310.

[21] Kalgutkar, A. S., and Marnett, L. J. (1994) Rapid inactivation of prostaglanidn endoperoxide synthases by N-(carboxyalkyl)maleimides. Biochemistry 33, 8625-8628.

[22] So, O. -Y., Scarafia, L. E., Mak, A. Y., Callan, O. H., and Swinney, D. C. (1998) The dynamics of prostaglandin H synthases. Studies with prostaglandin H synthase 2 Y355F unmask mechanisms of time-dependent inhibition and allosteric activation. J. Biol. Chem. 273, 5801-5807.

[23] Bhattacharyya, D. K., Lecomte, M., Rieke, C. J., Garavito, M., and Smith, W. L. (1996) Involvement of arginine 120, glutamate 524, and tyrosine 355 in the binding of arachidonate and 2-phenylpropionic acid inhibitors to the cyclooxygenase active site of ovine prostaglandin endoperoxide H synthase-1. J. Biol. Chem. 271, 2179-2184.

[24] Greig, G. M., Francis, D. A., Falgueyret, J. P., Ouellet, M., Percival, M. D., Roy, P., Bayly, C., Mancini, J. A., and O'Neill, G. P. (1997) The interaction of arginine 106 of human prostaglandin G/H synthase-2 with inhibitors is not a universal component of inhibition mediated by nonsteroidal anti-inflammatory drugs. Mol. Pharmacol. 52, 829-838.

[25] Loll, P. J., and Garavito, R. M. (1995) The structural basis of aspirin activity inferred from the crystal structure of inactivated prostaglandin H2 synthase. Nat. Struct. Bio. 2, 637-643.

[26] Loll, P. J., Picot, D., Ekabo, O., and Garavito, R. M. (1996) Synthesis and use of iodinated nonsteroidal anti-inflammatory drug analogs as crystallographic probes of the prostaglandin H2 synthase cyclooxygenase active site. Biochemistry. 35, 7330-7340.

[27] Malkowski, M. G., Ginell, S. L., Smith, W. L., and Garavito, R. M. (2000) The productive confromation of arachidonic acid bound to prostaglandin synthase. Science 289, 1933-1937.

[28] Luong, C., Miller, A., Barnett, J., Chow, J., Ramesha, C., and Browner, MF. (1996) Flexibility of the NSAID binding site in the structure of human cyclooxygenase-2. Nat. Struct. Biol. 3, 927-933

Bisogno, T., Melck, D., De Petrocellis, L., & Di Marzo, V. (1999) *J. Neurochem.* 72:2113-2119.

DuBois, R N, Radhika, A, Reddy, B S, Entingh, A J. (1996) *Gastroenterology* 110:1259.

Cohen, et al. U.S. Pat. No. 5,589,575, *Purification of hapten-carrier generated antibodies.*

Cayman Chemical, 1180 E. Ellsworth Road, Ann Arbor, Mich. 48108; 800-364-9897; *Prostaglandin $E_2$ affinity purification kit*, Catalog No. 514018.

Devane W A, Hanus L, Breuer A, Pertwee R G, Stevenson L A, Griffin D, Mandelbaum A, Etinger A, & Mechoulam R (1992) *Science* 258:1946-1949.

Eberhart, C E, Coffey, R J, Radhika, A, et al. (1994) *Gastroenterology* 107:1183.

Fosslien, E. (2000) *Ann. Clin. Lab. Sci.* 30:3-21.

Jeon, Y J, Yang, K H, Pulaski, J T, & Kaminski, N E. (1996) *Mol. Pharmacol.* 50:334-341.

Kalgutkar, A S, Kozak, K R, Crews, B C, Hochgesang, Jr. G P, & Marnett, L J. (1998) *J. Med. Chem.* 41: 4800-4818.

Landino, L M, Crews, B C, Timmons, M D, Morrow, J D, & Marnett, L J. (1996) *Proc. Natl. Acad. Sci. USA* 93:15069-15074.

MacPherson, J C, Pavlovich, J G, & Jacobs, R S. (1996) *Biochim. Biophys. Acta* 1303:127-136.

McCafferty, J., Hoogenboom, H., & Chiswell, D. (1996) *Antibody Engineering, a Practical Approach*, IRL Press@Oxford University Press.

Mernaugh, R. & Mernaugh, G. (1994) *Methods for the Production of Monoclonal Antibodies*, in Molecular Methods in Plant Pathology, Ed by RP Singh and US Singh, pg. 343-365.

Odenwaller, R, Chen, Y-NP., & Marnett, L J. (1990) *Methods. Enzymol.* 187: 479-485.

Sheehan, K M, Sheahan, K, O'Donoghue, D P, et al. (1999) *JAMA* 282:1254.

Sheng, H, Shao, J, Kirkland, S C, et al. (1997) *J. Clin. Invest.* 99:2254.

Stella, N., Schweitzer, P., & Piomelli, D. (1997) *Nature* 388:773-778.

Tsujii, M, Kawano, S, Du Bois, R N. (1997) *Proc. Natl. Acad. Sci. USA* 94:3336.

Vane, J R, Mitchell, J A, Appleton, I, Tomlinson, A, Bishop-Bailey, D, Croxtall, J, & Willoughby, D A (1994) *Proc. Natl. Acad. Sci. USA* 91:2046-2050.

Wadleigh, D J, Reddy, S T, Kopp, E, Ghosh, S, & Herschman, H R (2000) *J. Biol. Chem.* 275:6259-6266.

Yu, M, Ives, D, & Ramesha CS (1997) *J. Biol. Chem.* 272:21181-21186.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the claims following the detailed description of the invention. The present invention is not bound by theory or mechanism. Thus, although there have been described particular embodiments of the present invention of a new and useful "Method for in vitro and in vivo determination of COX-2 activity", it is not intended that such references be construed as limitations upon the scope of this invention except as set forth in the following claims.

We claim:

1. A method of detecting COX-2 enzymatic activity in a subject, comprising:
   a. obtaining a sample of the subject;
   b. detecting an amino acid eicosanoid metabolite in the sample, wherein the presence of the amino acid eicosanoid metabolite indicates the enzymatic activity of the COX-2 enzyme of the subject, wherein the amino acid eicosanoid metabolite is PGH2-Gly or HETE-Gly metabolite.

2. The method of claim 1, wherein the sample is urine.

3. The method of claim 1, wherein the sample is selected from the group consisting of blood, plasma, cerebrospinal fluid, saliva, bile, sputum, joint fluid, biopsy, and media from a cell culture.

4. The method of claim 1, wherein the amino acid eicosaniod metabolite is detected based on oxygenation of N-arachidonylglycine.

5. The method of claim 1, wherein the detecting step comprises generating mass spectrum.

6. A method of detecting enzymatic activity of COX-2 in a subject, comprising:
   a. obtaining a sample of the subject; and
   b. detecting a COX-2 specific metabolite of N-arachidonylglycine selected from the group consisting of PGH2-Gly and HETE-Gly wherein said metabolite comprises an eicosanoid, wherein the presence of the metabolite in the sample indicates the enzymatic activity of COX-2 in the subject.

7. The method of claim 6, wherein the eicosanoid is at least one of PGH2-glycine and HETE-Gly.

8. The method of claim 6, wherein the sample comprises urine.

9. The method of claim 6, wherein the sample is selected from a group consisting of urine, plasma, cerebrospinal fluid, saliva, sputum, bile, joint fluid, biopsy, and conditioned media from a cell culture.

10. The method of claim 6, wherein the detecting step comprises generating a mass spectrum of the metabolite.

* * * * *